United States Patent
Krummen et al.

(10) Patent No.: US 8,578,755 B2
(45) Date of Patent: Nov. 12, 2013

(54) DEVICE FOR PROVIDING GASES, IN PARTICULAR FOR ISOTOPIC RATIO ANALYSIS

(75) Inventors: Michael Krummen, Bad Zwischenahn (DE); Hans-Juergen Schlueter, Bremen (DE)

(73) Assignee: Thermo Fisher Scientific (Bremen) GmbH, Bremen (DE)

( * ) Notice: Subject to any disclaimer, the term of this patent is extended or adjusted under 35 U.S.C. 154(b) by 561 days.

(21) Appl. No.: 12/668,011

(22) PCT Filed: Jul. 1, 2008

(86) PCT No.: PCT/EP2008/005363
§ 371 (c)(1),
(2), (4) Date: Apr. 29, 2010

(87) PCT Pub. No.: WO2009/007042
PCT Pub. Date: Jan. 15, 2009

(65) Prior Publication Data
US 2010/0212398 A1  Aug. 26, 2010

(30) Foreign Application Priority Data
Jul. 6, 2007 (DE) .......................... 10 2007 031 680

(51) Int. Cl.
*G01N 1/22* (2006.01)
*H01J 49/00* (2006.01)

(52) U.S. Cl.
USPC .......................... 73/23.37; 73/23.42; 250/288

(58) Field of Classification Search
USPC ..................... 73/863.31, 23.37, 23.41, 23.42; 436/161; 250/281, 288
See application file for complete search history.

(56) References Cited

U.S. PATENT DOCUMENTS

| | | | | |
|---|---|---|---|---|
| 3,589,171 A * | 6/1971 | Haley | .......................... | 73/23.42 |
| 3,945,797 A * | 3/1976 | Mlinko et al. | ................... | 436/59 |
| 4,099,923 A * | 7/1978 | Milberger | ........................ | 422/80 |
| 4,139,439 A * | 2/1979 | Manuccia et al. | ............ | 204/164 |
| 5,012,052 A * | 4/1991 | Hayes | ............................. | 250/288 |
| 5,661,038 A | 8/1997 | Brenna et al. | | |
| 5,959,297 A * | 9/1999 | Weinberg et al. | ............... | 506/12 |
| 6,227,034 B1 * | 5/2001 | Trochesset | ................... | 73/23.42 |
| 6,701,774 B2 * | 3/2004 | Srinivasan et al. | ........... | 73/23.42 |
| 6,968,729 B1 * | 11/2005 | Karlsson et al. | ............ | 73/23.41 |
| 8,402,814 B2 * | 3/2013 | Hatscher et al. | ............. | 73/23.37 |
| 2002/0014106 A1 * | 2/2002 | Srinivasan et al. | ........... | 73/23.42 |
| 2002/0045265 A1 * | 4/2002 | Bergh et al. | ..................... | 436/37 |
| 2002/0170976 A1 * | 11/2002 | Bergh et al. | ................... | 236/49.1 |
| 2005/0257600 A1 * | 11/2005 | Karlsson et al. | ............. | 73/23.41 |
| 2011/0086430 A1 * | 4/2011 | Krummen et al. | ............ | 436/161 |

FOREIGN PATENT DOCUMENTS

EP  0 419 167 A1  9/1990
WO  WO 97/23779 A1  12/1996

OTHER PUBLICATIONS

English Translation of the Written Report of the International Search Authority (Jan. 6, 2010).*

* cited by examiner

*Primary Examiner* — Lisa Caputo
*Assistant Examiner* — Punam Roy
(74) *Attorney, Agent, or Firm* — Charles B. Katz; Nicholas Cairns

(57) ABSTRACT

A device is provided for delivering gases to an analyzer, such as an isotopic ratio mass spectrometer. The device includes first and second reactors, preferably arranged in parallel. At least one of the reactors may be selectively activated, or means may be incorporated to circumvent one of the reactors, such that different types of gas conversions may be achieved.

36 Claims, 9 Drawing Sheets

DEVICE FOR PROVIDING GASES, IN PARTICULAR FOR ISOTOPIC RATIO ANALYSIS

FIELD OF THE INVENTION

The invention relates to an apparatus having an analyzer and having a device for providing gases for an analysis, in particular for determining isotopic ratios, wherein the analyzer is connected downstream of the device and the device for providing the gases has a first gas path for a gas stream, a second gas path and a first reactor between the two gas paths, and wherein the first reactor has an inlet side and an outlet side and the inlet side of the first reactor faces the first gas path.

BACKGROUND OF THE INVENTION

A preferred, but not exclusive, application of the invention is that of measuring the isotopic ratios of gases or of substances that have first been transformed into the gas phase. It is known in this connection for various analyzers to be used, such as for example mass spectrometers (MS), accelerator MS, optical spectrometers (for example laser-resonance measurement), scintillation counters, etc. Preferred analyzers are mass spectrometers, such as for example multi-collector sector-field MS, time-of-flight mass spectrometers (TOF-MS) or quadrupole MS, in particular specifically for the determination of isotopic ratios. The invention is preferably used for measuring methane or respiratory gas, for example, and/or for determining the isotopic ratios of carbon, oxygen, nitrogen, sulfur, phosphorus, water vapor/deuterium or chlorine in suitable or appropriately prepared samples. The following molecules may be measured for this: $N_2$, $CO$, $O_2$, $H_2$, $CO_2$, $N_2O$, $CH_4$ and/or $NO_2$. This list is not exhaustive.

In the analyzer, simplest possible gases—one- to three-atom gases with only one or two different atoms—are measured. In a specific implementation, gases with more complex molecules may also be analyzed. More complex molecules are generally transformed into simpler molecules before the analysis, by pyrolysis, oxidation and/or reduction. Corresponding reactors or furnaces, or combinations of furnaces, are provided for this purpose.

Starting materials for the analyses are often liquids or gas mixtures, the constituents of which are separated from one another over time in a gas chromatograph.

Altogether, the apparatus used comprising the gas chromatograph, furnaces for gas conversion and the analyzer is quite complex. In particular in the area of gas conversion, the arrangement of the individual component parts of the apparatus can be varied in many ways. A slightly different construction is required for virtually every type of conversion. For the user, this is laborious and susceptible to error.

SUMMARY OF THE INVENTION

The object of the present invention is to provide a device for providing gases for an analysis in which different measurements are possible without changing the construction. In particular, it is intended that different gas conversions can be carried out with the device.

The apparatus according to the invention is characterized by at least one second reactor, which is arranged parallel to, or in series with, the first reactor, wherein at least one of the reactors can be deactivated or means are provided for circumventing at least one of the reactors.

The second reactor allows additional or alternative thermal measures to be applied to the gases supplied, so that different measurements are possible one after the other in an extremely short time. The reactors may be arranged and connected parallel to one another, for example with interconnected inlet sides or outlet sides. Preferably, the inlet sides of the reactors are interconnectable and so are the respective outlet sides. Furthermore, a common gas path may be provided for the supply of the gases to the two reactors. Finally, a common gas path may also be provided for the passing on of the gases from the two reactors in the direction of a downstream analyzing device.

An arrangement or connection of the reactors in series is also possible. This means that the inlet side of one reactor can be interconnected with the outlet side of the other reactor. During operation, both reactors or only one of the two reactors then operate(s). In addition, the reactors may have bypass lines, so that for example the gas can be made to bypass an inactive reactor.

Advantageously, the second reactor is arranged parallel to the first reactor, downstream of the first gas path, wherein switching devices for switching over the gas stream are provided in such a way that the gas stream coming from the first gas path, or a main part thereof, optionally passes into the first reactor or into the second reactor. Furthermore, a first switching device for switching over the gas stream may be provided. Preferably, only this single switching device for switching over the gas stream is provided. The switching has the effect that the gas stream passes into the first reactor by way of the inlet side thereof or into the second reactor by way of the inlet side thereof.

With the switching device provided, it is possible to switch back and forth between the two reactors for carrying out different gas conversions. The switching may be provided in such a way that the gas stream in the first gas path is made to pass completely via the first reactor or the second reactor. Alternatively, a division of the gas stream may take place in such a way that a large part of the gas stream is made to pass via one reactor and a small fraction of the gas stream is made to pass via the other reactor. Maintaining at least a small gas stream in the reactor helps to avoid dead volumes, inactive times and resultant measuring errors and hysteresis effects. The limiting case of dividing the gas stream in half between the reactors is of course also possible. A continuous gas flow through the reactors is also desired.

According to a further idea of the invention, the first switching device is provided between the second gas path and the outlet sides of the two reactors. Accordingly, the switching device is arranged downstream of the reactors. A simple branching arrangement may be provided upstream of the reactors, between the first gas path and the two reactors, so that gas can always pass into the two reactors. An advantage of this solution is that any high gas temperatures that may occur upstream of the reactors do not heat up the switching device. Furthermore, a steady flow through both reactors can be obtained. During switching, there are then no inactive times and there is no need to allow for dead volume. Finally, contamination of the switching device by analytes that are still organic upstream of the reactors is avoided.

Preferably, the first switching device is arranged in such a way that it optionally connects the second gas path to the first reactor or to the second reactor, to be precise to an outlet side of the respective reactor.

Alternatively, the switching device may of course also be arranged upstream of both reactors, and would then be arranged between the first gas path and the inlet sides of the reactors. This would then easily allow the effect to be achieved that only one of the two reactors is steadily flowed through by the gas.

According to a further idea of the invention, a third gas path and a second switching device are provided, wherein the second switching device optionally connects the third gas path to the first reactor or to the second reactor. Preferably, the switching takes place in such a way that the third gas path is connected to the first reactor or second reactor instead of the second gas path, to be precise on the outlet side of the reactors.

According to a further idea of the invention, the first switching device is combined with the second switching device to form a single switching device. Preferably, a multiway valve (4/2-way valve) is provided, arranged between the two reactors on the one hand and the two gas paths on the other hand (second and third gas paths), and assignment of each of the two reactors to one of the two gas paths is made possible.

According to a further idea of the invention, the third gas path has a different, in particular higher, flow resistance than the second gas path. The ratio of the mass flows or volume flows in the gas paths can be set by way of the flow resistance. The flow resistance may be formed as a constant or variable restriction. As a result, the volume flow along the gas paths can be controlled and can be changed continuously or abruptly. This avoids fractionating effects during the switching of the gas paths.

Preferably, the flow resistance in the third gas path is realized by a defined constriction or a valve or a constriction with an adjustable cross section. Preferred is an embodiment in which only a very small proportion is made to pass by way of the third gas path, for example only 5% of the volume flow, while 95% flows through the second gas path.

According to a further idea of the invention, it is provided that the two reactors are arranged in series one behind the other in such a way that an outlet side of one reactor is connected or can be connected to an inlet side of the other reactor, and that preferably at least one of the two reactors is provided with a bypass line which can optionally be connected to the other reactor, respectively. It is also possible for both reactors to have a bypass line. As a result, it is possible to make the gas optionally pass by one of the reactors and be thermally treated in the other reactor, respectively. A solution without a bypass line is also possible, however. The gas would then pass through both reactors one after the other and be thermally treated either only in one of the reactors or in both one after the other. Preferably, higher temperatures are provided in the second reactor in the direction of flow than in the first reactor. The arrangement may also be reversed, however. The same temperatures may also be provided.

According to a further idea of the invention, the reactors are arranged parallel to one another, wherein an additional gas source and switching devices are provided in such a way that optionally one of the two reactors is connected between the first gas path and the second gas path and the other reactor is connected to the additional gas source. This construction is advantageous in particular for the regeneration of the reactors. For example, a regenerating gas may flow from the additional gas source into the reactor, while the other reactor, respectively, is used for the preparation of gases for analysis. Instead of regeneration, a simple flushing operation may also be provided. The additional gas source may alternatively be arranged upstream or downstream of the reactors.

According to a further idea of the invention, it is provided that the first gas path leads to the first reactor, that a further gas path leads to the second reactor and that a dedicated gas source, in particular a dedicated gas chromatograph or a dedicated gas chromatography column, is arranged upstream of each of the gas paths. As a result, each reactor receives gas from a dedicated source. The sources or gas chromatographs may provide gases independently of one another.

According to a further idea of the invention, the first switching device or a further switching device may be provided between the inlet sides of the two reactors and the first gas path. The two reactors may also be each assigned a switching device on their inlet sides and their outlet sides. As a result, it is possible to carry out the switching optionally in the region of the inlet sides or the outlet sides.

According to a further idea of the invention, the first gas path is provided with a connecting location for a branch. The branch can then be used for a return flow of the gas or backflushing of the reactors. In this way, the gas arriving in the first gas path can be discharged before it enters the reactors. If a switching device is arranged in the region of the inlet sides of the reactors, the connecting location for the branch also lies upstream of the switching device.

According to a further idea of the invention, the second gas path is provided with a connecting location for a branch, in particular for connection to a gas supply. The same may also be provided for the third gas path. Gases for the backflushing of the reactors or for other purposes may be introduced by way of the branches. Oxygen for regenerating an oxidation reactor or helium as an additional carrier gas may be supplied in this way.

According to a further idea of the invention, the reactors can be heated up to different temperatures, in particular for pyrolysis on the one hand and oxidation on the other hand. Depending on the application, different reactions may be desired.

According to an independent aspect of the invention, the reactors are arranged in a common housing with at least partly common insulation. On account of the high temperatures, the reactors are surrounded by a heat-insulating wall. To minimize the heat that is lost, the reactors are arranged adjacent one another, so that they thermally influence one another or the lost heat of the hotter reactor contributes to the heating up of the cooler reactor. The reactors are at least partly surrounded by a common insulating wall.

According to a further idea of the invention, the housing has at least one insulating layer with an outer side and an inner side, one of the reactors being arranged closer to the outer side than the other reactor. Ambient temperature prevails on the outer side of the housing. There is a temperature gradient from the outer side to the hottest reactor. The less hot reactor is arranged along the temperature gradient.

Preferably, at least one of the two reactors is arranged in the insulating layer. As a result, a distinct change in temperature can also be achieved between the two reactors. The hotter reactor is then preferably provided in a chamber surrounded by the insulating layer.

Both reactors may be assigned thermocouples for controlling corresponding heaters. Both reactors may also each be assigned at least one heater. The reactors may then be heated up independently of one another. Alternatively, it is also possible for only one heater to be provided, in particular within the chamber surrounded by the insulating layer, either for both reactors together or for one reactor, so that the other reactor is heated by the lost heat.

According to a further idea of the invention, both reactors are each assigned at least one heater, the heater provided for the reactor that is arranged closer to the outer side being less powerful than the heater of the other reactor. The inner reactor (greater distance from the outer side) is then provided with the main heater, while the outer heater has only a supplementary heater. The desired temperatures are preferably a minimum of 800° C. (outer reactor) and a maximum of 1600° C. (inner reactor).

According to a further idea of the invention, the device has an interface for the connection of an optical detector or a mass spectrometer, in particular an isotope mass spectrometer. Such an interface may be, for example, an open split. Other interfaces are also possible. Preferably, the interface is arranged downstream of the second gas path or is connected to it.

According to a further idea of the invention, a third reactor is provided, arranged along the second gas path, in particular a reduction reactor. This may be operated in particular in connection with an oxidation reactor as the first or second reactor.

Advantageously, the first gas path has a connecting location with a branch or a line to a detector. The connecting location may be switchable by a valve—also in the line itself—or a restriction on the line. With the aid of the detector before the gases enter the reactors, additional measurements can be carried out.

According to a further idea of the invention, the gas paths are at least partly formed by inertized metal lines. The lines are usually capillaries. These are, for example, produced from metal and inertized on the inner wall. Such lines are robust with respect to thermal and mechanical stress. In particular, lines of steel or high-grade steel with special coatings are used. Corresponding material combinations are known under the trade names Silcosteel, SilcInert, MXT and others.

A typical reactor is a thin tube that is heated from the outside and in which the gas molecules are oxidized, reduced or react in some other way after being supplied with heat. The reactor tube is arranged in a furnace with an insulating wall or is pushed into the furnace. Arranged upstream of the reactor there may be a gas chromatograph or other separating device, which breaks down the individual constituents of a sample over time and so gradually supplies them to the reactor tube. The arrangement of a gas chromatograph/separating device following on after the reactors, for separating the reaction products over time, is also possible.

For carrying the gases to the reactor tube and following on after the reactor tube, relatively thin lines are provided. For the sake of simplicity, these lines and the usually comparatively thicker reactor tube are referred to hereafter as capillaries and must be connected to one another in a gastight and reliable manner to achieve reproducible results. Screw connections between the capillaries, in particular where the gases enter the reactor tube and where they leave the same, have been customary so far. The screw connections can be easily released and make it possible for individual capillaries to continue to be when the other capillaries, respectively, that were previously connected are exchanged. One disadvantage of the screw connections or other releasable connections in this area is the great risk of leakage, for instance caused by temperature fluctuations and the breaking off of the thin tubes during assembly.

Advantageously, the capillaries are connected to one another by bonding, adhesion or pressing. A soldered connection to metal or previously metallized surfaces is also within the scope of the invention. The types of connection mentioned are intended to lead to a gastight and preferably non-releasable connection of the capillaries. When the capillary-like reactor tube is exchanged, the capillaries respectively connected to it, which are generally thinner, are also exchanged at the same time. The costs thereby incurred for the thinner capillaries are negligible, or even overcompensated by the then obviated screw connections. The new solution is not only more reliable than the known solution but may also be less costly.

According to a further idea of the invention, the capillaries have different diameters and overlap one another, at least with end regions, the end regions being connected to one another (in the region of the overlap or part of the same). The different diameters make it possible to push the capillaries to be connected into one another and so achieve an overlap.

Advantageously, the capillaries are connected to one another two-dimensionally. The strength and gastightness of the connection are thereby increased. "Two-dimensionally" means that bonding, adhesion or pressing occurs in more than just a punctiform or linear manner. In particular, "two-dimensionally" relates to an extent in the axial direction and at the same time in the circumferential direction.

At least one of the capillaries may consist of ceramic material. In particular, the capillary-like reactor tube, or at least the inner surface thereof, consists of a ceramic material, for example in the case of an $H_2$ reactor. At least a great heat resistance is an advantage.

Advantageously, at least one of the capillaries consists at least partly of quartz glass, in particular an outer and/or inner surface, for example in the case of an $H_2$ reactor. Synthetic quartz glass or silica glass, also known as fused silica, are particularly well suited. So called Silcosteel capillaries are also well suited.

According to a further idea of the invention, it is provided that the overlapping region has at least one bonding connection or adhesive connection in the region of a coating of one of the capillaries. Bonding agents or adhesive agents are distributed all around the capillary, i.e. in the circumferential direction. In particular, these are gastight bonding agents or adhesive agents. An example of a gastight adhesive is a polyimide-based adhesive. Different adhesives may also be provided in different temperature zones, for example one adhesive for the stability of the connection and one adhesive for the sealing.

According to a further idea of the invention, it is provided that the overlapping region has at least one bonding connection or adhesive connection in the region outside the coating. Here, too, the bonding agent or adhesive agent is preferably provided all around, the agents used being particularly heat-resistant. "Heat resistant" in this sense means that the connection is preserved even at temperatures of 300° C. to 400° C. or more, for example at more than 600° C. to 800° C. or even over 1000° C.

Advantageously, at least one of the capillaries consists at least partly of nobel metal. This is in particular copper, ruthenium, rhodium, palladium, silver, rhenium, osmium, iridium, platinum or gold. Adequate strength is important for the corresponding application area. Non-nobel metals may also be used with preference, for example nickel, in particular for reactor tubes. Metallic or metallized capillaries may preferably also be soldered.

Advantageously, one of the capillaries is provided in the overlapping region with a platinum surface and the other capillary is provided with a ceramic surface preferably in the case of a $CO_2$ reactor. Of course, the two capillaries may also respectively consist completely of platinum or ceramic material. Platinum is relatively soft in comparison with the ceramic material and, when under pressure—by pressing—fills the rough surface of the ceramic material, so that a particularly intimate and gastight connection is produced.

Advantageously, at least one of the capillaries is provided with an inertized surface, in particular on the inside. A reaction with the gas flowing through and/or bonding agent or adhesive agent is then unlikely. A capillary is inertized for example with a Silcosteel coating. Other less reactive surfaces, such as for example platinum, are also favorable.

According to a further idea of the invention, a furnace for the thermal treatment of gases is provided, wherein a reactor tube similar to a capillary and a heater are arranged in a furnace and an insulation is provided, with the reactor tube and/or a capillary being led through the insulation, and wherein the reactor tube and the capillary are connected to one another. The reactor tube has in this case the function of a capillary and is connected in the sense described above to the (other) capillary. Preferably, the reactor tube is respectively connected at both its ends to a thinner capillary.

According to a further idea of the invention, the capillary connected to the reactor tube has an outer coating, in particular of a non-heat-resistant material, preferably such as polyimide, the coating being removed where the capillary reaches into the insulation from the outside. The high temperature prevailing inside the furnace decreases perpendicularly to the insulation up to the outer side. In order as far as possible not to expose the coating to thermal stress, removal of the same to the outside of the insulation of the furnace is advantageous. In this case, there may also be overlapping between the thinner capillary and the reactor tube in the region of the removed coating. The coating is preferably produced from polyimide. Assumed here as heat-resistant is a material that withstands temperatures of at least 300° C., preferably also over 400° C., without reacting and/or significantly losing strength.

Advantageously, the apparatus according to the invention is provided with an analyzer, in particular a mass spectrometer, connected downstream of the device. In this case, a gas chromatograph may be connected upstream of the device. This gas chromatograph is then connected upstream of the first gas path.

BRIEF DESCRIPTION OF THE DRAWINGS

Further features of the invention otherwise emerge from the description and from the claims. Advantageously exemplary embodiments of the invention are explained in more detail below on the basis of drawings, in which:

DETAILED DESCRIPTION OF EMBODIMENTS OF INVENTION

Figure 1:
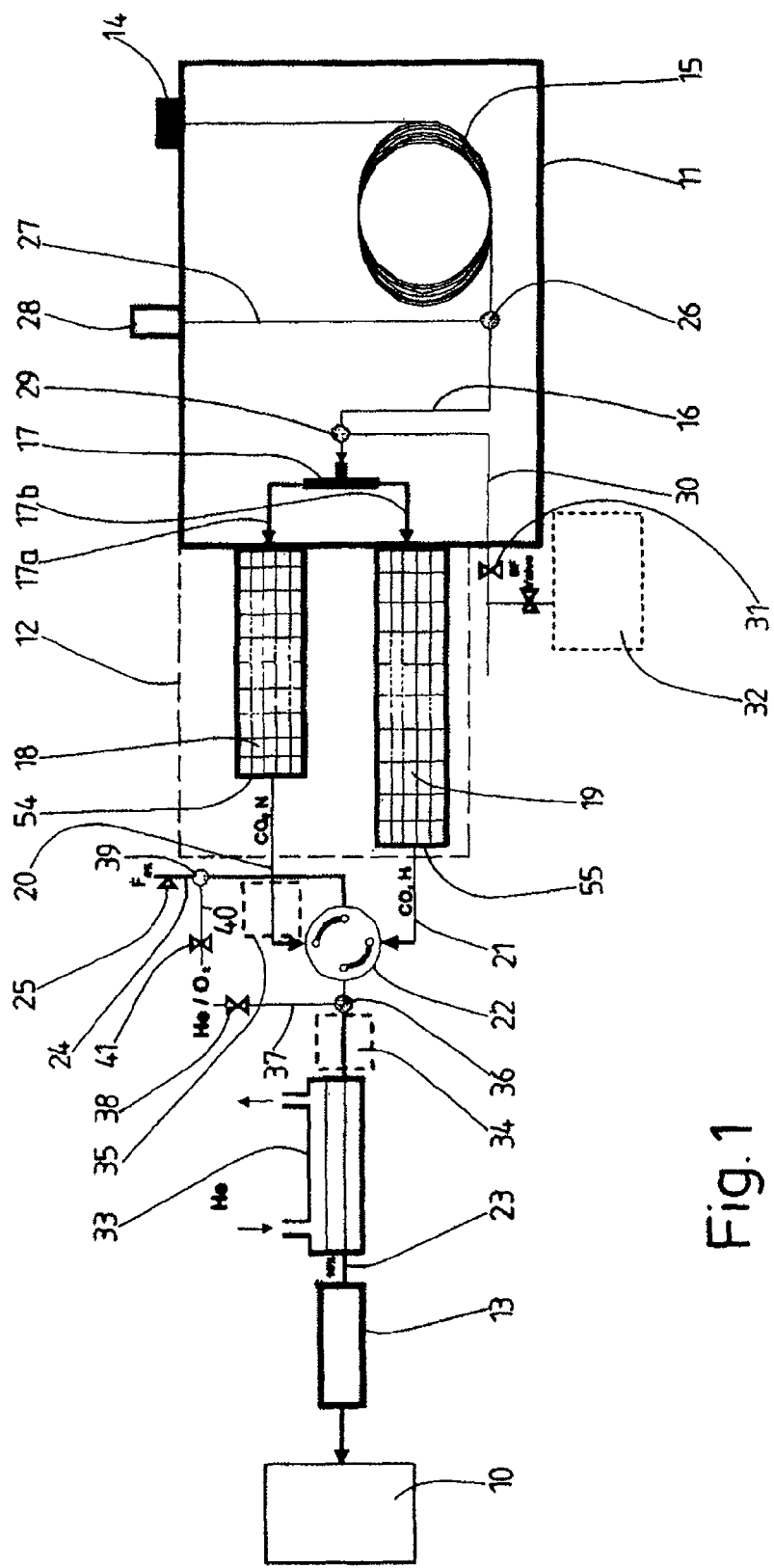
FIG. 1 shows a schematic representation of an apparatus according to the invention.

For the analysis of gases in a detector 10, in particular a mass spectrometer for determining isotopic ratios, a gas sample coming from a gas chromatograph 11 is passed through a furnace 12 and fed to the detector by way of an interface 13, for instance an open split.

From a GC column 15 connected to an injector 14, a first gas path 16 leads by way of a branching arrangement 17 (T piece) and branches (gas paths) 17a, 17b to inlet sides of two reactors 18, 19 arranged parallel to one another in the furnace 12. Lines (gas paths) 20, 21 lead from the outlet sides of the reactors 18, 19 out of the furnace 12 to a common switching device 22, which is formed here as a 4/2-way valve.

The valve (the switching device 22) allows the reactors 18, 19 to be optionally connected to a second gas path 23 or alternatively to a third gas path 24. The second gas path 23 leads to the interface 13, while the third gas path 24 is provided with a defined restriction 25, so that the third gas path 24 has a much greater flow resistance than the second gas path 23.

The terms "inlet sides" and "outlet sides" refer to a main direction of flow, that is from the gas chromatograph 11 to the detector 10. The individual gas paths, lines and branches are formed in particular as capillaries. The reactors 18, 19 are also preferably capillary-like tubes or reactor tubes.

Figure 2:
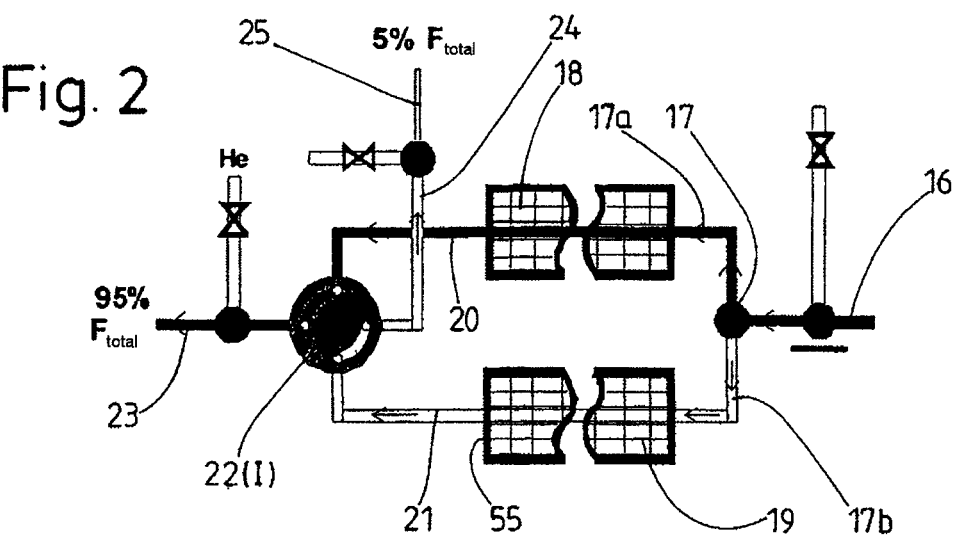
FIG. 2 shows part of an apparatus according to FIG. 1 with a switching device switched in a certain way.
Figure 3:
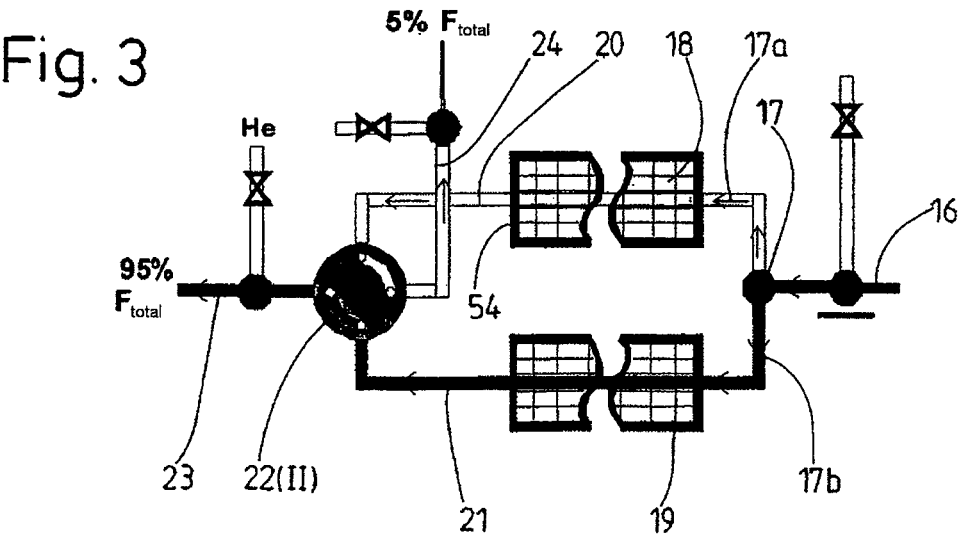
FIG. 3 shows the detail according to FIG. 2, but in a different switching position of the switching device.

The two switching positions of the switching device 22 are reproduced in FIGS. 2 and 3. According to FIG. 2, in a switching position I of the switching device 22, the gas is fed from the first gas path 16 to the high-temperature reactor 18 (oxidation reactor) and passes from there by way of the switching device 22 into the second gas path 23. By contrast, in this switching position I, the reactor 19 that is not heated as strongly (pyrolysis reactor) is connected to the third gas path 24. In theory, the gas coming from the first gas path 16 can flow via both reactors 18, 19 and pass either into the second gas path 23 or the third gas path 24. In fact, due to the restriction 25 (as a cross-sectional constriction), there is a clear disequilibrium in the distribution of the volume flows in favor of the second gas path 23. Only 5% to 10% of the gas passes into the third gas path 24. Consequently, in this switching position I, the gas flowing via the reactor 18 ultimately passes into the detector 10. A configuration of the device or the restriction with a smaller disequilibrium of the volume flows up to a 50:50 distribution is also possible. With increasing secondary flow, the signal amplitude at the detector becomes smaller.

In the other switching position II of the switching device 22, the two reactors 18, 19 are likewise connected to the second gas path 23 and the third gas path 24, but in exactly the opposite way to that previously described. Consequently, in the switching position II, the gas flowing via the reactor 19 passes by way of the second gas path 23 to the detector 10. Here, too, approximately 5% of the total amount of gas flows via the other reactor (here the reactor 18) into the third gas path 24.

Depending on the application and construction of the reactors, the gas streams may also be divided between different reactors 18, 19 in such a way that one of the reactors is regenerated by the gas stream while the sample is thermally treated in the other reactor. The regeneration may also refer, for example, to the buildup of layers of carbon.

To extend the functions, the apparatus optionally has additional component parts:

In the first gas path 16, a branching arrangement 26 with a branch 27 to a detector 28 may follow on after the GC column 15. This detector is either an additional detector or the branch 27 is merely a bypass and leads to the detector 10 while circumventing the furnace 12. The numbers 28 and 10 would then refer to the same component.

A further branching arrangement 29 is fitted into the first gas path 16, in particular between the branching arrangements 17 and 26. The branching arrangement 29 leads by way of a branch 30 and a valve 31 out of the GC 11. Optionally, a volume-flow measuring device 32 is provided to follow on after the valve 31.

A water trap 33, in which the moisture present in the gas stream is separated and carried away, is provided in the second gas path 23. Preferably, a separation of the moisture may take place at a water-permeable membrane with a carrier gas counterflow. Helium is preferably used as the carrier gas.

A further reactor 34, in particular a reduction reactor, may be provided in the second gas path 23, in particular arranged upstream of the water trap 33. This further reactor may operate together with one of the reactors 18, 19, so that for example an oxidation and reduction of the flowing gases can be carried out one after the other. In addition or alternatively, a further reactor 35 may be arranged along the line 20. This is also preferably a reduction reactor.

The second gas path 23 may have a branching arrangement 36 with a branch 37 and a connection or valve 38 for a gas source. For example, helium or some other inert gas that can be used for backflushing or regenerating the reactors may be fed in by way of the branch 37. Preferably, some or all of the branching arrangements are switchable, so that the gas paths can be exactly set. Backflushing is then possible, for example, in the switching position according to FIG. 1 via the lower reactor 19 and the branch 30. It is also possible for a counter pressure to be produced in the second gas path 23 by opening the valve 38, so that the gas coming from the GC column 15 does not pass into the reactors 18, 19 but is separated by way of the branch 30. For example, it may be advisable not to direct solvent peaks into the reactors and/or detectors. The valves, for example valve 38, for opening and closing a line or a branch may also have a further switching position, that is a leakage position to avoid pressure increases.

The third gas path 24 may have a branching arrangement 39, which may be connected to a gas source by way of a branch 40 and a valve 41. Preferably, the provision of gas for the regeneration of the oxidation reactor 18 is envisaged here. Suitable gases are oxygen, methane, etc. If and when required, the other reactor 19 may also be optionally regenerated with a substance connected to the valve 41.

For the measurements, the gases or substances may be brought together with carrier gas, for example with helium or hydrogen, in particular before they enter the GC 11 or at some other desired location.

Figure 4:
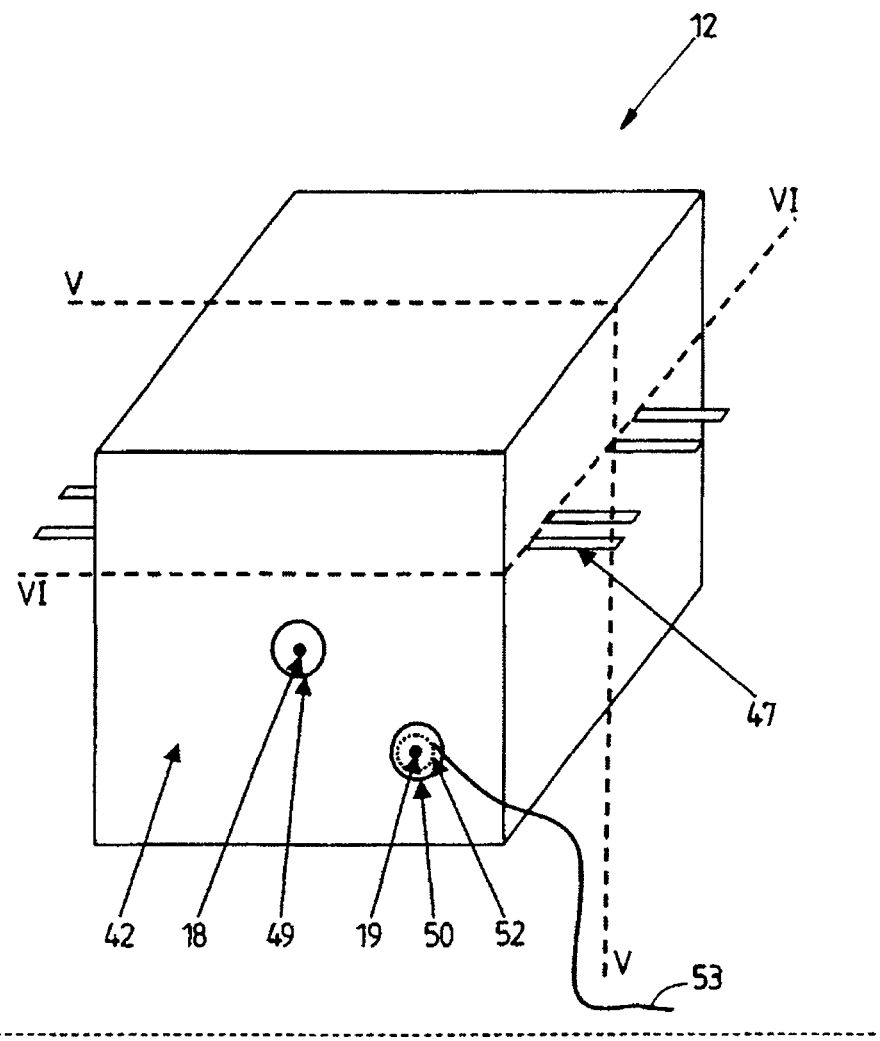
FIG. 4 shows a furnace with two reactors in a perspective representation.

The construction of the furnace 12 with the reactors 18, 19 is explained in more detail below on the basis of FIGS. 4 to 6:

The furnace 12 may be of a substantially cuboidal form. Other external configurations are possible. A housing 42 is provided on the inside with a thick insulation 43. Depending on the stability of the insulating layer 43, the housing 42 may also be omitted. The number 42 then refers to the outer side of the insulating layer 43.

Formed in the furnace 12 is a chamber or a furnace space 44, which is empty or filled with insulating material, for example mineral wool, perlite or other temperature-resistant substances. Arranged in the furnace space 44 are heating elements 45, 46, the supply lines 47, 48 of which—which may at the same time be mountings—are led through the insulating layer 43.

The reactors 18, 19 are thin, capillary-like tubes, in particular of ceramic, and preferably run transversely through the furnace 12 parallel to one another at a distance and horizontally directed. In this case, the reactors 18, 19 may be respectively surrounded by a protective tube 49, 50, in particular of metal or some other material that conducts heat as much as possible.

Figure 6:
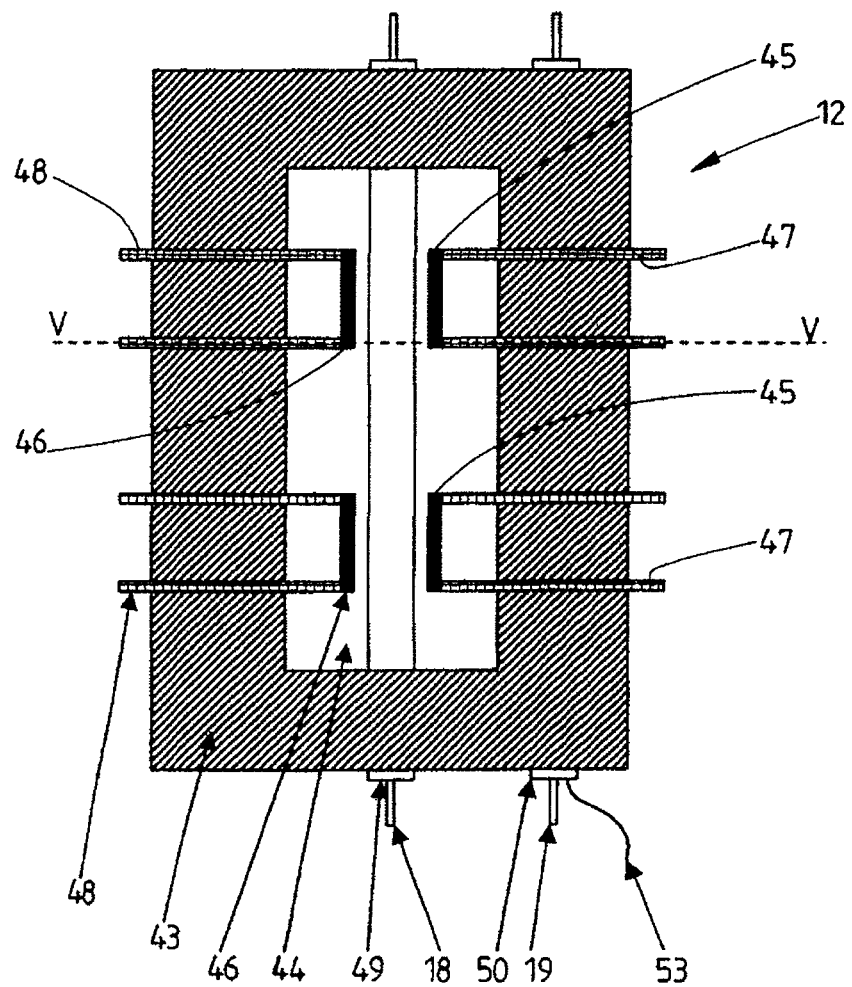
FIG. 6 shows the furnace according to FIG. 5 in a horizontal section.

The reactors 18, 19 and protective tubes 49, 50 extend through the insulating layer 43 and protrude slightly beyond the housing 42, or the outer side of the insulating layer 43, the reactors 18, 19 somewhat further than the protective tubes 49, 50, see FIG. 6.

The reactor 18 is provided here as a high-temperature reactor and is heated by the heating elements 45, 46 on sides lying opposite one another, and at the same time over a number of portions of its length. Correspondingly, two pairs of heating elements 45, 46 are depicted in FIG. 6. In this case, the heating elements 45, 46 and the reactor 18 are arranged completely within the furnace space 44.

The reactor 19 runs within the insulating layer 43, that is between an inner side 51 of the same and the housing 42 or the outer side. In the present case, the reactor 19 is arranged in the region of a transition between an upright wall and a bottom wall of the insulating layer 43.

Figure 5:
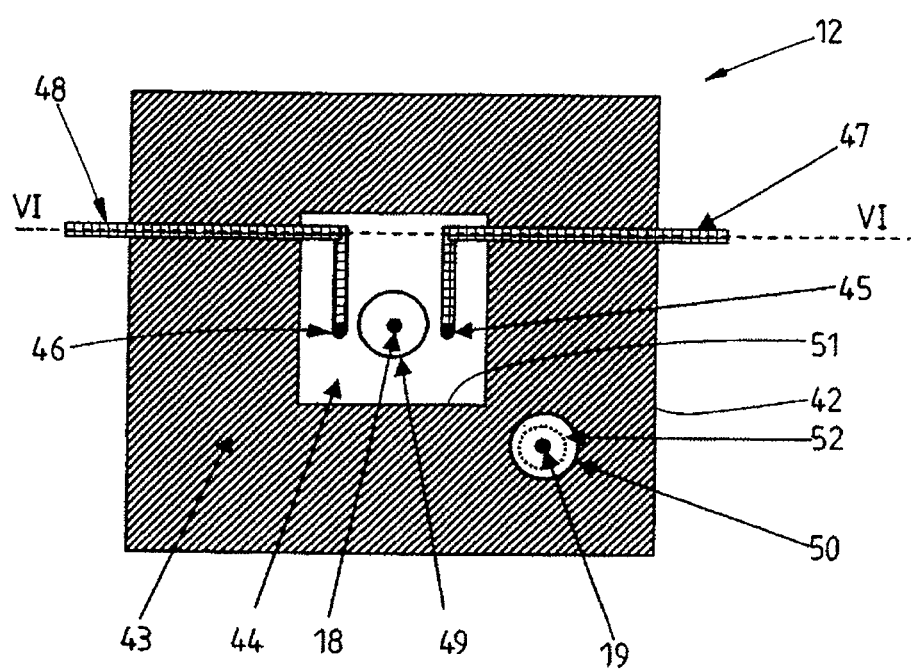
FIG. 5 shows the furnace according to FIG. 6 in a vertical section.

In the present case, the reactor 19 is provided with a supplementary electrical heater 52, see FIG. 5. This is arranged in the protective tube 50. A corresponding electrical supply line 53 is laid in the intermediate space between the reactor 19 and the protective tube 50, see FIG. 6.

During operation, the temperature of the reactor 18 is set by the heating elements 45, 46. Temperature sensors that are not shown may be provided for this purpose. Some of the heat also passes to the reactor 19, which as a result is heated slightly less than the reactor 18. If an exact temperature setting is desired for the reactor 19, this can be carried out by means of the supplementary heater 52. Without the effect of the supplementary heater, the temperature of the reactor 19 is determined by the power of the heating elements 45, and the position of the reactor 19 within the insulating layer 43 together with the outside temperature. In the most favorable case, it is possible to dispense with the operation of the supplementary heater 52.

The supply lines 47, 48 are preferably laid approximately horizontally in an upper region of the furnace space 44 and angled away there in the downward direction, so that the heating elements 45, 46 lie approximately halfway up the furnace space 44, as does the reactor 18.

The insulating layer 43 preferably consists of ceramic fiber blocks, mineral wool, chamotte or other materials with good heat insulation.

The reactors 18, 19 are connected to the capillary-like lines 17a, 17b and 20, 21 by suitable connecting elements, bonding, adhesion or pressing. This is explained in more detail below on the basis of FIGS. 1 and 7 with the alternatives a) and b).

In the gas chromatograph (GC column 15), the substances contained in a sample are separated from one another over time. In the subsequent furnace 12, an oxidation, reduction, gasification or pyrolysis takes place. The temperatures occurring lie distinctly above the ambient temperature that otherwise acts on the apparatus.

The gaseous substances are carried in the capillary-like lines 16, 17a, 17b, 20, 21 (FIG. 1). These consist of synthetic quartz glass, which is also referred to as fused silica. A composite with other materials is possible. Preferably, however, here the lines consist exclusively of synthetic quartz glass with a coating.

In another embodiment, the lines are produced from metallic material, in particular from high-grade steel, which has a surface coating for the purpose of inertization. Coatings for steels or high-grade steels are known by the name Silcosteel (registered trademark).

Figure 7:
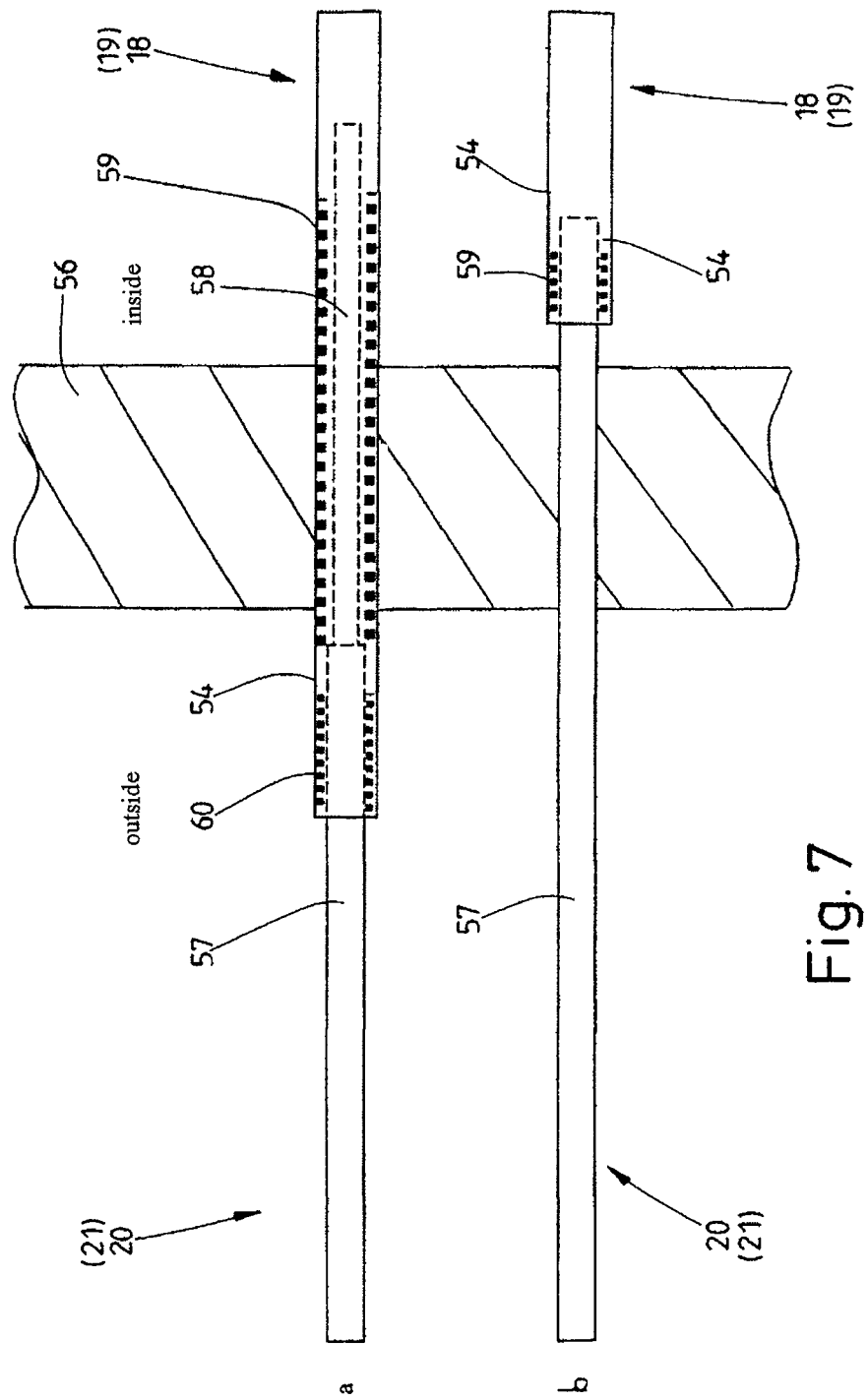
FIG. 7 shows alternatives a) and b) for a bonding connection of capillaries in the region of a heat-insulating furnace wall.

Capillaries are likewise provided within the furnace 12, that is the reactor tubes 18, 19, the ends 54 of which emerge from the furnace 12, see FIG. 7 alternative a). The reactor tubes 18, 19 usually consist of a ceramic material and, depending on the application, are heated up to approximately 800° C. to 1600° C. Substances that are consumed or can be reactivated may be provided in the reactor tubes to promote the oxidation, pyrolysis or other reactions. A thermally assisted reduction of gaseous substances is also possible in the furnace 12.

In the case of known solutions, the lines are connected to the ends of the reactor tubes by screw connections. The aim of this is to make it possible for the reactor tube to be exchanged while retaining the lines. The known screw connections may, however, cause problems that disturb the analysis considerably. For instance, leaks or dead volumes may occur (in particular in the case of difficulties during assembly).

Instead of the known solution, in the case of the present exemplary embodiment according to the invention the line 20 is connected to the adjacent end 54 of the reactor tube 18 non-releasably, in particular by direct bonding. Known adhesives, in particular high-temperature adhesives, are suitable as bonding agents. The bonding agents may be selected on the basis of the desired properties, such as grain size of the filler, temperature resistance, elasticity, thermal expansion, etc.

An embodiment with two adhesives of different properties is also preferred. A high-temperature adhesive provides for the connection to be of adequate strength. A further adhesive, for example with polyimide, increases the sealing. The sealing adhesive may also be subsequently injected into the first adhesive.

Instead of the bonding connection, a connection by adhesion may also be provided. In this case, agents for improving the adhesion may be used. Such agents may at the same time also be bonding agents.

The end 54 of the reactor tube emerges from a heat-insulating wall 56 of the furnace 12, and consists of a ceramic material. The line 20 is a fused silica capillary and is provided on the outside with a coating of polyimide. The coated part of the line 20 is provided in example a) of FIG. 7 with the number 57. The coating has been removed from one end 58 of the line 20, since here the coating is not heat-resistant. Here, the line 20 and the end 54 are bonded to one another twice, that is on the one hand with a first bonding location 59 between the non-coated end 58 and the end 54. In this case, the bonding location 59 preferably lies in the interior of the furnace 12 and is formed by a high-temperature adhesive. A second bonding location 60 is formed between the end 54 and the coated part 57 outside the wall 56. The bonding agent may be less heat-resistant here. Preferably, a bonding agent that is adapted to the properties of the coating, in particular a polyimide adhesive, is used.

The connection of the lines 17a, 17b to the reactor tubes 18, 19 may be formed by analogy with the previous embodiments. However, thermally insensitive materials are also to be preferred here for the lines 17a, 17b and the corresponding bonding agents because of the possible higher temperatures following the gas chromatograph 15.

On account of the described bonding between the lines and the reactor tubes, these connecting locations are reliable and durably tight. The reactor tubes and lines are connected to another non-releasably and, if and when required, are exchanged together. Releasable connections or branching arrangements are provided for this purpose between the lines 17a, 17b, 20, 21 on the one hand and the branching arrangement 17 or the switching device 22 on the other hand. Such releasable connections are known and do not require any further explanation. Alternatively, the lines may also be coupled to the gas chromatograph 15 on the one hand and the cooling trap 33 on the other hand, or to further component parts of the apparatus, by way of releasable connections.

If a highly heat-resistant line 20 is used, it may also be led through the wall 56 into the furnace 12 and end there, see example b) of FIG. 7. Correspondingly, here the end 54 of the reactor tube does not reach as far as the wall 56 in the interior of the furnace 12. The provided bonding location 59 is highly heat-resistant.

Figure 8:
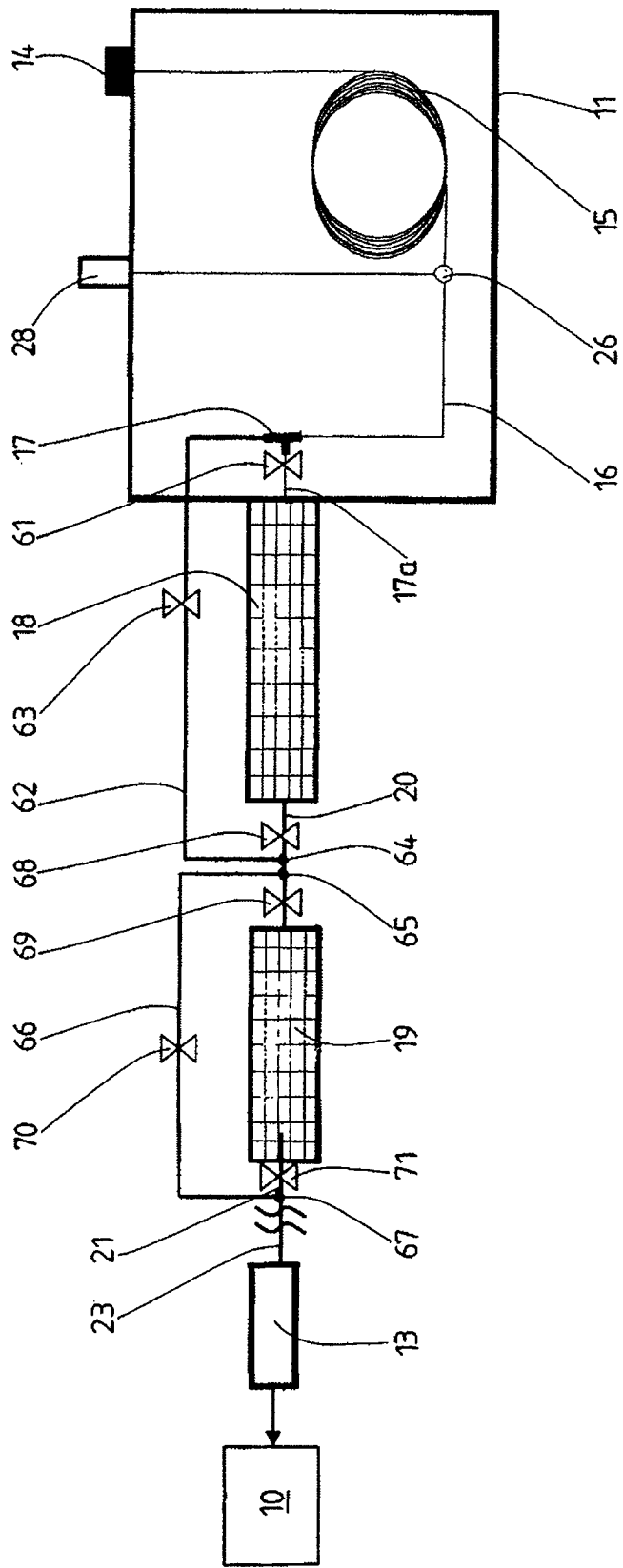
FIG. 8 shows a further embodiment of the apparatus according to the invention in a schematic representation analogous to FIG. 1.

FIG. 8 shows a series connection of the two reactors 18, 19. The reactor 18 is connected to the first gas path 16 by way of the branching arrangement 17. In the branch 17a there is an activatable valve 61. From the branching arrangement 17, a bypass line 62, provided with an activatable valve 63, runs parallel to the reactor 18.

The line 20 connects the reactor 18 to the second reactor 19 and has two branching arrangements 64, 65. The bypass line 62 opens out into the branching arrangement 64. From the branching arrangement 65, a further bypass line 66 runs parallel to the reactor 19 up to a branching arrangement 67 in the line 21 following the reactor 19.

Activatable valves are also provided between the reactor 18 and the branching arrangement 64 (valve 68), between the branching arrangement 65 and the reactor 19 (valve 69), in the bypass line 66 (valve 70) and between the branching arrangement 67 and the reactor 19 (valve 71).

In FIG. 8, only the interface 13 and the detector 10 are depicted as following on after the line 21. In fact, further component parts of the apparatus may be provided, for example the parts depicted in FIG. 1 between the switching device 22 and the interface 13.

With the device shown in FIG. 8, it is possible to feed the gas produced or provided optionally to one of the two reactors or even to both reactors one after the other. If appropriate, the inactive reactor is cooled. By way of the controlled valves, the gas may be made to pass by one or both of the reactors. Depending on the application and type of reactor, backflushing or outgassing processes may be prevented by the valves mentioned. In this case, the representation according to FIG. 8 is to be understood as being purely schematic. In fact, the two reactors may also be spatially arranged next to one another in parallel. The series connection of the reactors is then obtained by corresponding routing of the lines mentioned, in particular the line 20.

Figure 9:
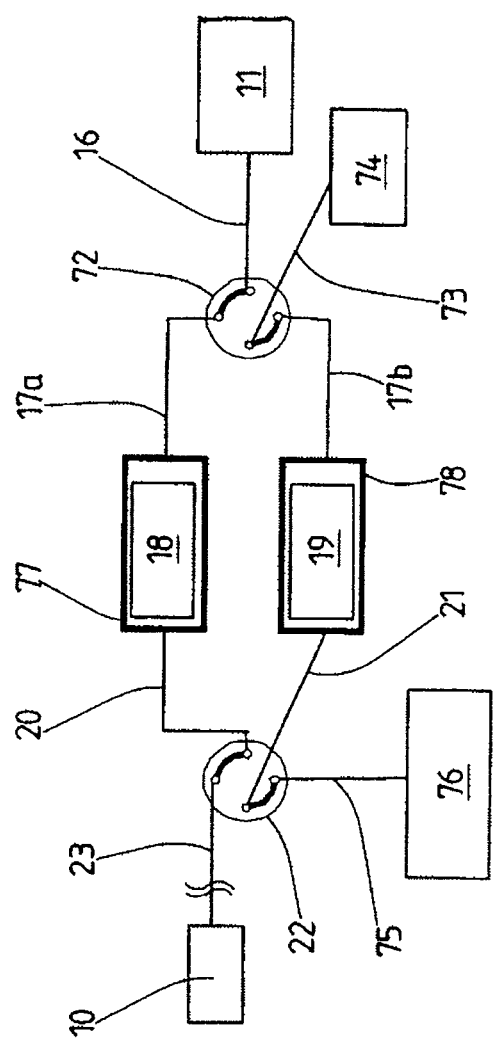
FIG. 9 shows a further embodiment of an apparatus according to the invention in a representation analogous to FIGS. 2 and 3.

FIG. 9 also shows special aspects with regard to the mode of operation and construction. Here, the two reactors 18, 19 are intended for alternating analyzing and regenerating operation. The switching device 22 that is also shown in FIG. 1 is arranged downstream of the two reactors. A switching device 72 with the same or similar functionality is also arranged upstream of the reactors 18, 19. In addition to the branches 17a, 17b, a gas source, for instance the gas chromatograph 11, is connected to the switching device 72 by way of the gas path 16, and a gas receiver 74, in particular for deposited gases that cannot be used any further and, for example, are to be filtered or chemically converted, is connected to said switching device by way of a further gas path 73.

A gas source 76, which preferably provides gas for the regeneration of the reactors 18, 19, for example in counterflow, is connected to the switching device 22 by way of a line 75. During operation, it is always possible to carry out an analysis with the inclusion of one of the reactors 18, 19, while a regeneration process takes place in the other reactor, respectively, and the gas thereby flowing in the opposite direction through the regenerating reactor is fed to the gas receiver 74. In FIG. 9, the lower reactor 19 is in the process of regenerating, while gas for the analysis is being thermally treated by the upper reactor 18. The gas to be analyzed passes by way of the switching device 22 into the second gas path 23 to the detector 10. Further component parts of the device of various functionalities may be provided along the gas path 23, for example by analogy with FIG. 1.

The two reactors 18, 19 may each be assigned dedicated furnaces with dedicated insulation 77, 78. Alternatively, the reactors 18, 19 may also be arranged in a common furnace with common insulation corresponding to the furnace 12 in FIG. 1.

Figure 10:
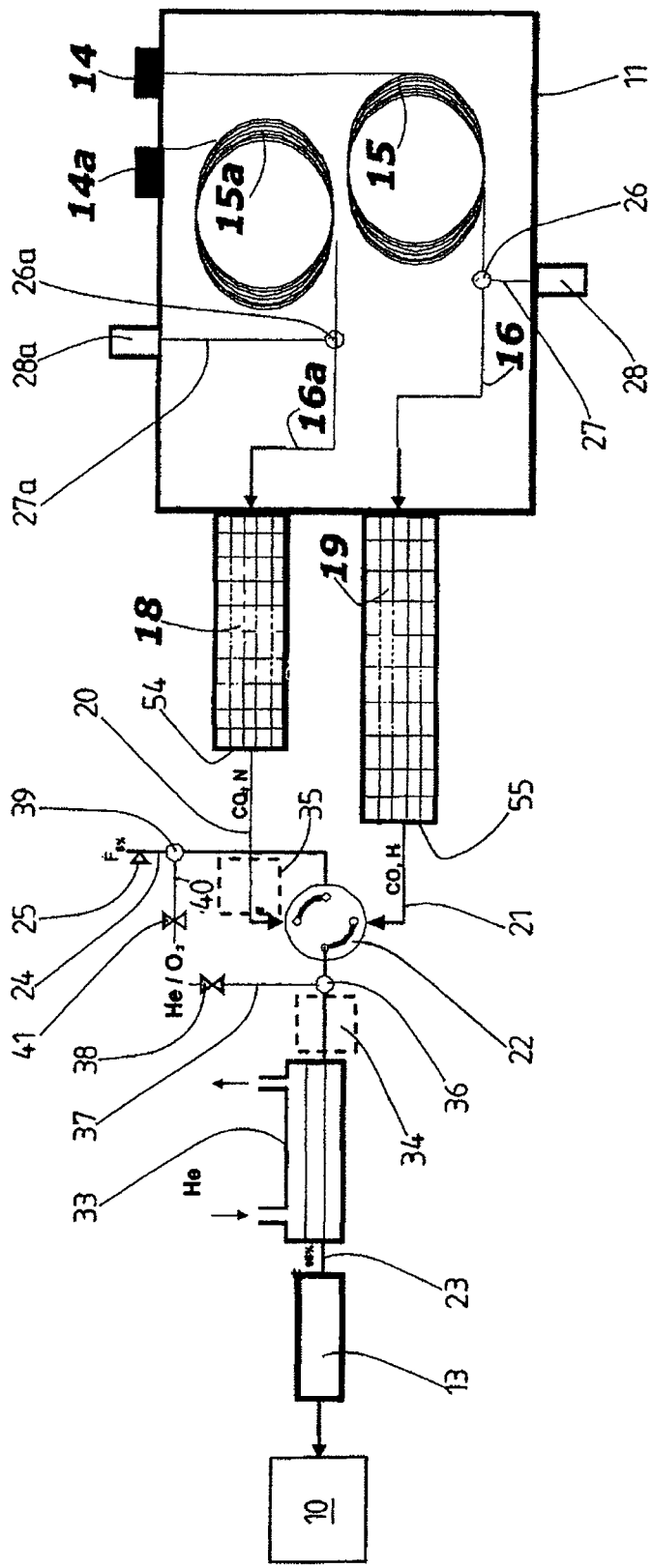
FIG. 10 shows a further embodiment of the invention in a representation analogous to FIG. 1.

In the embodiment according to FIG. 10, two gas chromatographs or one gas chromatograph 11 with two GC columns 15, 15a is/are arranged upstream of the two reactors 18, 19. The GC column 15 is connected to the reactor 19 by way of the gas path 16. In the gas path 16, the branching arrangement 26 with the branch 27 and the detector 28 is provided in a way corresponding to FIG. 1. Parallel thereto, the GC column 15a is connected to the reactor 18 by way of the gas path 16a. An injector 14a is arranged upstream of the GC column 15a. Furthermore, a branching arrangement 26a with a branch 27a and a connected detector 28a lies in the gas path 16a.

The two injectors 14, 14a with the GC columns 15, 15a may provide gas samples independently of one another.

In the embodiment according to FIG. 10, a switching device corresponding to the switching device 72 may be provided between the gas paths 16, 16a and the reactors 18, 19, as in FIG. 9, together with the branches 17a, 17b shown there. The GC columns 15, 15a may then be optionally connected to one of the two reactors 18, 19.

Instead of the GC 11 or the GC columns 15, 15a, other sources for the substances to be analyzed may also be provided, for example liquid chromatographs, evaporators, etc.

What is claimed is:

1. An apparatus comprising: a device for providing gases for analysis, the device having a first gas path for a gas stream, a second gas path, and a first reactor located between the first and second gas paths, the first reactor having an inlet side facing the first gas path and an outlet side, the device further having a second reactor; and at least one switching device that is switchable between first and second states, wherein switching the switching device to the first or second state selects gases that have passed through a respective one of the first or second reactors to flow to an isotope ratio analyzer arranged downstream of the device;
    wherein the second reactor is arranged parallel to the first reactor, downstream of the first gas path, and wherein the at least one switching device is configured and arranged such that the gas stream coming from the first gas path, or a main part thereof, passes into the first reactor or into the second reactor;
    wherein a first switching device for switching over the gas stream is provided in such a way that the gas stream coming from the first gas path, or a main part thereof, passes into the first reactor by way of the inlet side thereof or into the second reactor by way of an inlet side thereof;
    wherein the first switching device is provided between the second gas path and the outlet sides of the first and second reactors.

2. The apparatus as claimed in claim 1, wherein the at least one switching device connects the second gas path to the first reactor or to the second reactor.

3. The apparatus as claimed in claim 1, wherein the device further comprises a third gas path and a second switching device, wherein the second switching device connects the third gas path to the first reactor or to the second reactor, and wherein the third gas path has a higher flow resistance than the second gas path.

4. The apparatus as claimed in claim 3, wherein the flow resistance in the third gas path is realized by a defined constriction or a valve or a constriction with an adjustable cross section.

5. The apparatus as claimed in claim 1, wherein the second gas path is provided with a connecting location for a branch.

6. The apparatus as claimed in claim 1, wherein a third gas path is provided with a connecting location for a branch.

7. The apparatus as claimed in claim 1, wherein the first and second reactors are arranged in a common housing with at least partly common insulation.

8. The apparatus as claimed in claim 1, wherein the first and second reactors are each assigned at least one heater, and in that the heater provided for the reactor that is arranged closer to the outer side is less powerful than the heater of the other reactor.

9. The apparatus as claimed in claim 1, further comprising an interface for the connection of the analyzer wherein the analyzer is an optical detector or mass spectrometer.

10. The apparatus as claimed in claim 1, further comprising a third reactor, which is arranged along the second gas path.

11. The apparatus as claimed in claim 1, wherein at least one of the gas paths and the reactors are at least partly formed by capillaries, and in that the capillaries are connected to one another by one of bonding, adhesion or pressing.

12. The apparatus as claimed in claim 11, wherein at least one of the capillaries consists of ceramic material.

13. The apparatus as claimed in claim 11, wherein at least one of the capillaries consists at least partly of quartz glass.

14. The apparatus as claimed in claim 11, wherein at least one of the capillaries has an inertized surface.

15. The apparatus as claimed in claim 1, wherein the analyzer is a mass spectrometer arranged downstream of the at least one switching device.

16. An apparatus comprising: a device for providing gases for analysis, the device having a first gas path for a gas stream, a second gas path, and a first reactor located between the first and second gas paths, the first reactor having an inlet side facing the first gas path and an outlet side, the device further having a second reactor; and at least one switching device that is switchable between first and second states, wherein switching the switching device to the first or second state selects gases that have passed through a respective one of the first or second reactors to flow to an isotope ratio analyzer arranged downstream of the device;
    wherein the first gas path leads to the first reactor, in that a further gas path leads to the second reactor, and in that a dedicated gas source wherein the source is a dedicated gas chromatograph or a dedicated GC column is arranged upstream of each of the gas paths.

17. The apparatus as claimed in claim 16, wherein the at least one switching device connects the second gas path to the first reactor or to the second reactor.

18. The apparatus as claimed in claim 16, wherein the device further comprises a third gas path and a second switching device, wherein the second switching device connects the third gas path to the first reactor or to the second reactor, and wherein the third gas path has a higher flow resistance than the second gas path.

19. The apparatus as claimed in claim 18, wherein the flow resistance in the third gas path is realized by a defined constriction or a valve or a constriction with an adjustable cross section.

20. The apparatus as claimed in claim 16 further comprising an interface for the connection of the analyzer wherein the analyzer is an optical detector or mass spectrometer.

21. The apparatus as claimed in claim 16 wherein at least one of the gas paths and the reactors are at least partly formed by capillaries and in that the capillaries are connected to one another by one of bonding, adhesion or pressing.

22. The apparatus as claimed in claim 21 wherein at least one of the capillaries consists at least partly of ceramic material or quartz glass and/or has an inertized surface.

23. An apparatus comprising: a device for providing gases for analysis, the device having a first gas path for a gas stream, a second gas path, and a first reactor located between the first and second gas paths, the first reactor having an inlet side facing the first gas path and an outlet side, the device further having a second reactor; and at least one switching device that is switchable between first and second states, wherein switching the switching device to the first or second state selects gases that have passed through a respective one of the first or second reactors to flow to an isotope ratio analyzer arranged downstream of the device;
wherein the first gas path is provided with a connecting location for a branch.

24. The apparatus as claimed in claim 23, wherein the at least one switching device connects the second gas path to the first reactor or to the second reactor.

25. The apparatus as claimed in claim 23, wherein the device further comprises a third gas path and a second switching device, wherein the second switching device connects the third gas path to the first reactor or to the second reactor, and wherein the third gas path has a higher flow resistance than the second gas path.

26. The apparatus as claimed in claim 25, wherein the flow resistance in the third gas path is realized by a defined constriction or a valve or a constriction with an adjustable cross section.

27. The apparatus as claimed in claim 23 wherein a further switching device is provided between the inlet sides of the first and/or second reactor and the first gas path.

28. The apparatus as claimed in claim 23 further comprising an interface for the connection of the analyzer wherein the analyzer is an optical detector or mass spectrometer.

29. The apparatus as claimed in claim 23 further comprising a third reactor which is arranged along the second gas path.

30. The apparatus as claimed in claim 23 wherein the first gas path has a connecting location with a line to a detector.

31. The apparatus as claimed in claim 23 wherein at least one of the gas paths and the reactors are at least partly formed by capillaries and in that the capillaries are connected to one another by one of bonding, adhesion or pressing.

32. The apparatus as claimed in claim 31 wherein at least one of the capillaries consists at least partly of ceramic material or quartz glass and/or has an inertized surface.

33. An apparatus comprising: a device for providing gases for analysis, the device having a first gas path for a gas stream, a second gas path, and a first reactor located between the first and second gas paths, the first reactor having an inlet side facing the first gas path and an outlet side, the device further having a second reactor; and at least one switching device that is switchable between first and second states, wherein switching the switching device to the first or second state selects gases that have passed through a respective one of the first or second reactors to flow to an isotope ratio analyzer arranged downstream of the device;
wherein a gas chromatograph is arranged upstream of the first and second gas paths.

34. The apparatus as claimed in claim 33, wherein the at least one switching device connects the second gas path to the first reactor or to the second reactor.

35. The apparatus as claimed in claim 33, wherein the device further comprises a third gas path and a second switching device, wherein the second switching device connects the third gas path to the first reactor or to the second reactor, and wherein the third gas path has a higher flow resistance than the second gas path.

36. The apparatus as claimed in claim 35, wherein the flow resistance in the third gas path is realized by a defined constriction or a valve or a constriction with an adjustable cross section.

* * * * *